(12) United States Patent
Tomita et al.

(10) Patent No.: US 6,451,584 B2
(45) Date of Patent: *Sep. 17, 2002

(54) LACTOBACILLUS BIFIDUS GROWTH PROMOTING COMPOSITION AND USE THEREOF

(75) Inventors: Mamoru Tomita; Hirotoshi Hayasawa; Toshio Ohashi; Mitsunori Takase; Hirohiko Nakamura, all of Kanagawa; Koji Sayama, Hokkaido, all of (JP)

(73) Assignee: Morinaga Milk Industry Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/319,268

(22) PCT Filed: Oct. 28, 1997

(86) PCT No.: PCT/JP97/03915

§ 371 (c)(1), (2), (4) Date: Jun. 14, 1999

(87) PCT Pub. No.: WO98/26043

PCT Pub. Date: Jun. 18, 1998

(30) Foreign Application Priority Data

Dec. 12, 1996 (JP) .............................. 8-352359

(51) Int. Cl.$^7$ ................ C12N 1/20; C12N 1/00
(52) U.S. Cl. ............... 435/253.6; 435/252.1; 435/252.9; 435/822; 435/853
(58) Field of Search .......... 435/252.9, 252.1, 435/253.6, 822, 853

(56) References Cited

U.S. PATENT DOCUMENTS 4,782,045 A * 11/1988 Machida et al. .............. 514/23
5,294,546 A * 3/1994 Dombau et al. ............ 435/101

FOREIGN PATENT DOCUMENTS

| JP | 59-132884 | * | 7/1984 |
| JP | 5-103631 | * | 4/1993 |
| JP | 7-39318 | * | 2/1995 |

* cited by examiner

Primary Examiner—Sandra E. Saucier
Assistant Examiner—Vera Afremova
(74) Attorney, Agent, or Firm—Oblon, Spivak, McClelland, Maier & Neustadt, P.C.

(57) ABSTRACT

A *Lactobacillus bifidus* growth promoting composition which significantly grows *lactobacillus bifidus* and does not produce any side effect such as diarrhea, and a blend comprising the above composition and other edible ingredients, and the composition comprises at least one oligosaccharide selected among lactulose, fructo-oligosaccharide, and galacto-oligosaccharide, and raffinose as the active ingredients.

26 Claims, 1 Drawing Sheet

LACTOBACILLUS BIFIDUS GROWTH PROMOTING COMPOSITION AND USE THEREOF

TECHNICAL FIELD

The present invention pertains to a composition that can be orally administered to bring intestinal flora to a good state and efficiently control intestinal function, and the use thereof. In further detail, the present invention pertains to a *Lactobacillus bifidus* growth promoting composition which comprises 1 or 2 or more oligosaccharides selected from lactulose, galacto-oligosaccharide, and fructo-oligosaccharide, and raffinose as the active ingredients, and a blend which comprises the above-mentioned composition and other edible ingredients.

BACKGROUND ART

Approximately 100 species of microorganisms and 100 trillion or more individual microorganisms live in the human intestines and form the intestinal bacteria plexus. Intestinal bacteria, such as *Lactobacillus bifidus* and the like, have a strong relationship with the health of humans, and there are bacteria that are considered to have a beneficial effect on the body and bacteria that appear to generate putrefactive substances and carcinogens, etc., and have a detrimental effect on the body. The distribution of these flora varies with factors such as age, race, lifestyle and environment, diet, etc. Intestinal flora in particular are markedly affected by daily diet. Consequently, diet is very important in enhancing a function for controlling intestinal condition. Commercial milk products, such as yogurt, etc., containing *Lactobacillus bifidus* for balanced intestinal function have been widely used for years. By means of these products, viable lactic acid bacteria are ingested in order to balance intestinal function.

On the other hand, it is known that sugar sources are very important for intestinal *Lactobacillus bifidus* growth and various oligosaccharides that are known as *Lactobacillus bifidus* growth promoters are now being actively used. These oligosaccharides share in common the fact that they are not broken down by human digestive enzymes, they are not absorbed from the intestines, they are selectively assimilated by *Lactobacillus bifidus*, etc., and many oligosaccharides, including lactulose, various galacto-oligosaccharides, various fructo-oligosaccharides, isomalto-oligosaccharides, xylo-oligosaccharides, etc., are known.

These oligosaccharides have been used in the past in various foods, drugs, etc., for the purpose of forming *Lactobacillus bifidus*-rich intestinal flora, but they are individually (including mixtures of extracts from starting materials and synthetic reaction products) added or mixed (refer to Bifidus, vol. 6, pages 143~150, 1993, Bifidus, vol. 8, pages 1~5, 1994, Japanese Patent No. 2,549,638, Japanese laying open Patent No. 8-256730, etc.). Moreover, the function of these oligosaccharides varies with the type of oligosaccharide and there is a large difference in the extent to which they are assimilated by *Lactobacillus bifidus* and putrefying bacteria (for instance, Clostridium, etc.). Furthermore, when they are individually used in a product, only the characteristics of the individual oligosaccharide can be realized and sufficient *Lactobacillus bifidus* growth is not always obtained. Therefore, thus far measures for effectively realizing good balance of intestinal function have not been established.

That is, the following 2 points are important in realizing effective intestinal function balancing activity as a *Lactobacillus bifidus* growth promoting sugar source.

(1) The sugar source is widely assimilated by the main *Lactobacillus bifidus* present in the intestines.

(2) The sugar source will not be assimilated by the intestinal putrefying bacteria, or the amount of sugar source that is assimilated by the intestinal putrefying bacteria is low, and the growth (consumption) rate of *Lactobacillus bifidus* is as fast as possible.

Consequently, it was not known in the past that combining oligosaccharides provides good *Lactobacillus bifidus* growth promoting effects when compared to the individual use of oligosaccharides, and there was a need for a *Lactobacillus bifidus* growth promoting sugar source with which the ability to balance intestinal function can be realized.

DISCLOSURE OF THE INVENTION

Figure 1:
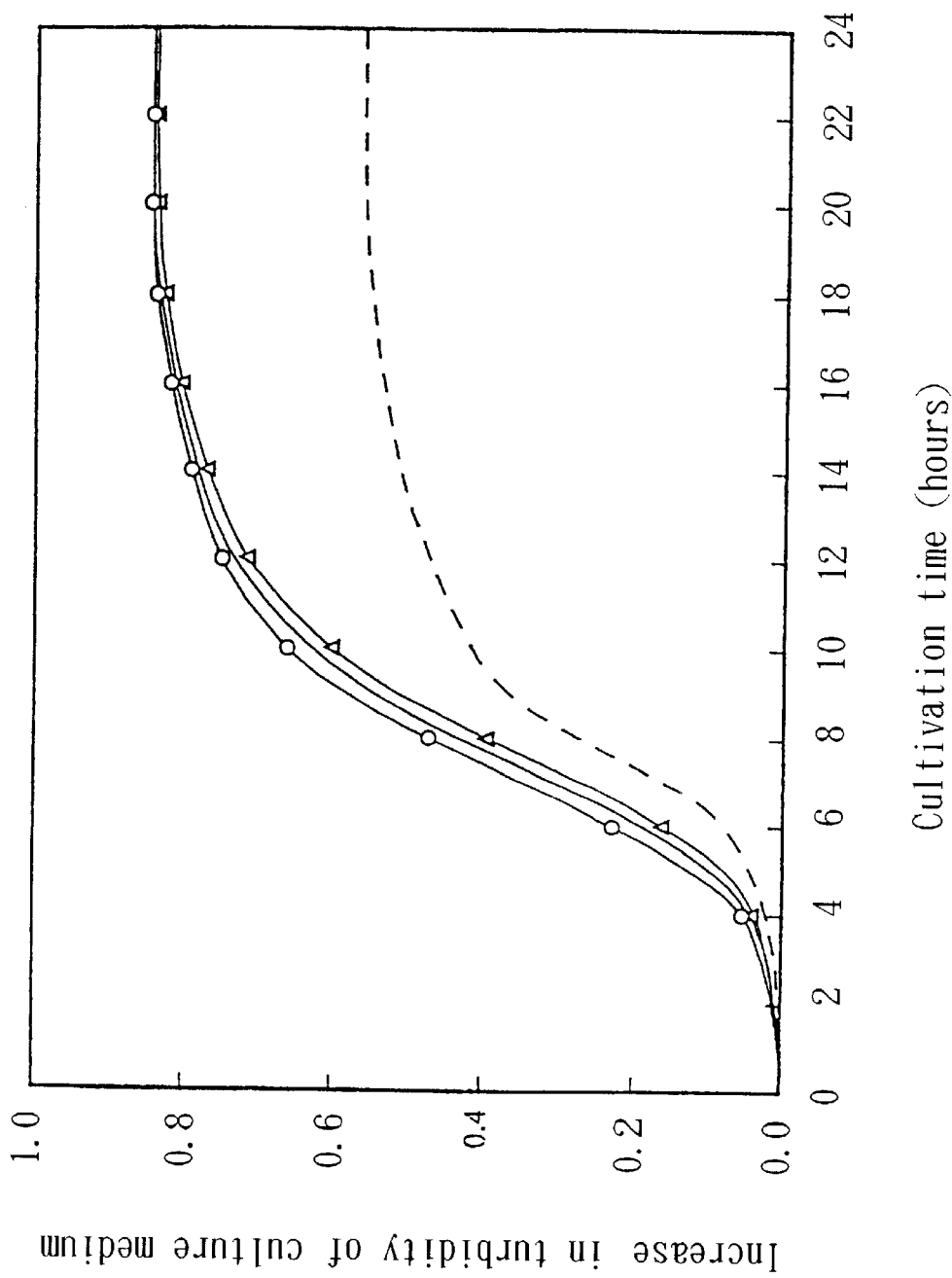
FIG. 1. The FIG. 1 shows the correlation between cultivation time and the increase in medium turbidity.

The inventors repeatedly performed intense studies in light of the above-mentioned background art and completed the present invention upon discovering that a composition obtained by combining raffinose and specific oligosaccharides each at specific ratios, and a blend containing said composition and other edible ingredients, have a marked effect on growth of *Lactobacillus bifidus* and as a result, intestinal function is effectively balanced when compared to the conventional use of individual oligosaccharides.

The purpose of the present invention is to present a *Lactobacillus bifidus* growth promoting composition that markedly grows *Lactobacillus bifidus* and has no adverse reactions, such as diarrhea, etc.

Another purpose of the present invention is to present a blend that contains the above-mentioned *Lactobacillus bifidus* growth promoting composition and other edible ingredients.

The first part of the present invention that solves the above-mentioned problem is a *Lactobacillus bifidus* growth promoting composition which comprises 1 or 2 or more oligosaccharides selected from the group consisting of lactulose, fructo-oligosaccharide, and galacto-oligosaccharide, and raffinose as the active ingredients, and the preferred embodiment is at least 1 part (weight) oligosaccharide to 9 parts (weight) raffinose.

The second part of the present invention that solves the above-mentioned problem is a blend comprising 1 or 2 or more oligosaccharides selected from the group consisting of lactulose, fructo-oligosaccharides and galacto-oligosaccharides, raffinose, and other edible ingredients, and in the preferred embodiments, the other edible ingredients are ingredients normally used for food products, the other edible ingredients are ingredients of powdered milk for nursing babies, and the other edible ingredients are nutritive agents.

The *Lactobacillus bifidus* growth promoting composition that is the first part of the present invention will first be explained.

The product produced by conventional methods from beet sugar (for instance, Japanese laying open Patent No. 54-49345, etc.) can be used as the raffinose that is used in the present invention, for instance, or the crude product that is made and sold as soy oligo-saccharide (Japan Food Science, vol. 26, No. 10, p.56–64 (1987)) can also be used directly as a "raffinose-containing" oligosaccharide. Furthermore, raffinose that is produced directly from soy whey by conventional methods (for instance, Japanese laying open Patent No. 59-179064, etc.) can be used.

Moreover, the lactose used in the present invention can be lactose produced by alkali isomerization by conventional methods in any preparation form, such as syrup, powder, granules, etc., but in order to minimize adverse reactions, it is preferred that the lactose be produced by the method in, for instance, Japanese publication Patent No. 52-21063.

Moreover, 1-kestose, nystose, etc., can be given as examples of the fructo-oligosaccharides used in the present invention, and they can be made from sucrose solution, etc., by conventional methods (for instance, Japanese laying open Patent No. 8-173109 and Japanese publication Patent No. 59-53834).

Furthermore, compounds represented by the following general formula (1)

Gal–(Gal)$n$–Glc (1)

(Here, Gal in the formula is a galactose residue, Glc is a glucose residue, and n is an integer of 1~4.) can be used as the galacto-oligosaccharide, and they can be produced from lactose solution by conventional methods (for instance, Japanese publication Patent No. 58-20266, etc.).

By means of the present invention, there is at least 1 part (by weight; the same below) of 1 or 2 or more oligosaccharides selected from the group consisting of lactulose, fructo-oligosaccharides and galacto-oligosaccharide per 9 parts raffinose, which are the above-mentioned active ingredients, and it is preferred that they be mixed within a range of from 1 part oligosaccharide to 4 parts raffinose to 2 parts oligosaccharide to 3 parts raffinose. Moreover, the composition of these oligosaccharides should be administered within a range of 0.01 to 0.5 g/day per 1 kg body weight, and the final composition should contain 0.05% (by weight; the same below unless otherwise stated) or more, when it is ingested by humans.

The *Lactobacillus bifidus* growth promoting composition of the present invention contains as its active ingredients raffinose and other specific oligosaccharides, but preservatives, excipients, etc., can be added by conventional methods in order to improve shelf life and to control the preparation form.

Next, the blend that is the second part of the present invention will be described. The blend that is the 2nd part of the present invention consists of the above-mentioned *Lactobacillus bifidus* growth promoting composition that is the first part of the present invention and other edible ingredients. The other edible ingredients include proteins, lipids, sugars, vitamins and minerals, etc., and these other edible ingredients can be mixed as needed at the desired ratio with the above-mentioned *Lactobacillus bifidus* growth promoting composition that is the first part of the present invention to make various foods, powdered milk for nursing, various nutritive agents, etc., by conventional methods. The mixture of the present invention can be made in any conventional form, such as liquid, powder, granules, etc.

Actual examples of the other edible ingredients are listed below. Examples of proteins are milk protein, soy protein, wheat flour, corn protein, etc., or decomposition products of proteins, peptides, amino acids, etc.

Moreover, the lipids can be a variety of conventional prepared oils and fats, oil and fat compositions, fatty acid compositions, and various saccharides, such as oligosaccharides other than the above-mentioned oligosaccharides, glucose, sucrose, dextrose, starches, etc., can be used as the sugar.

Furthermore, examples of minerals that are added are sodium chloride, potassium chloride, calcium chloride, magnesium sulfate, calcium glycerophosphate, iron citrate, etc., and examples of vitamins that are added are vitamin A, vitamin $B_1$, vitamin $B_2$, vitamin $B_6$, vitamin $B_{12}$, niacin, folic acid, vitamin C, vitamin D, vitamin E, vitamin K, calcium pantothenate, nicotinamide, choline chloride, etc.

In addition, various additives, including guar gum, pectin, locust bean gum, carrageenan, etc., as stabilizers, benzoic acid and its salts, sorbic acid and its salts, etc., as preservatives, somachin, stevioside, saccharin, amino acid derivatives, lactitol, etc., as sweeteners, and polyphenols, β-carotene, ascorbic acid derivatives, etc., as oxdizing agents, can be added. When necessary, bacterial bodies, conventional excipients, extenders, emulsifiers, fragrances, coloring agents, preservatives, etc., can further be added.

As is later explained, the *Lactobacillus bifidus* growth promoting composition of the present invention that is produced as described above and the blend containing the above-mentioned composition effectively promote growth of *Lactobacillus bifidus*, improving the intestinal environment and fecal characteristics and manifesting the ability to balance intestinal function when compared to the conventional use of individual oligosaccharides of various types.

The present invention will now be explained in detail while referring to test examples.

As previously mentioned, a fast consumption rate in terms of use by *Lactobacillus bifidus* is an essential condition for sugar sources that promote the growth of *Lactobacillus bifidus*. Consequently, the increase in turbidity of the cultivation medium due to growth of bacterial bodies was used in order to measure utilization of saccharide by the *Lactobaccilus bifidus* as a method that provides relatively good reproducibility over cultivation time.

PRELIMINARY TEST 1

This test was performed in order to investigate changes over time in medium turbidity and determine if measurement of turbidity after a certain cultivation time is valid for assessing the speed with which the *Lactobacilluls bifidus* consumes sugar:

(1) Bacterial Strains Tested

*Bifidobacterium longum* BB-536, which is a microorganism belonging to the genus Bifidobacterium, derived from humans that was separated and identified from the feces of healthy adults by conventional methods (Tomonari Mitsuoka, ed., "Research of Bifidus Bacteria," pages 40~60, Zaidanhojin Nihon Bifizusukin Senta (Japan Bifidus Bacteria Center), 1994) was used in this test. Furthermore, this strain is stored by the inventors and is available for any person as needed.

(2) Test Method

1) Preparation of basic medium and pre-cultivation solution

A liquid medium consisting of 0.5% yeast extract, 0.5% meat extract, 2% glucose, 0.1% potassium monophosphate, 0.1% potassium diphosphate, 0.2% anhydrous sodium acetate, 0.05% cystine, 0.05% Tween 80, and 96.5% purified water (ion-exchanged water) was sterilized under high pressure at 115° C. for 15 minutes and used as the basic medium.

Ten milliliters of the above-mentioned basic medium were poured into a test tube and the sterilized test tube medium was inoculated with 1 platinum loop from the stored slant culture of the above-mentioned *Lactobacillus bifidus*. Two milliliters sterile liquid paraffin were applied over this to establish anaerobic conditions. Then 24-hour anaerobic cultivation was performed to obtain the pre-cultivation solution.

2) Preparation of test medium

Culture mediums were made using lactulose (Morinagaka Milk Industry Co., Ltd.), raffinose (Nihon Tensai Seito Co., Ltd.), and isomalto-oligosaccharide (Hayashibara Shoji Co., Ltd.), in place of the glucose in the basic medium. Ten milliliters were poured into each test tube and sterilized to obtain the test culture medium.

3) Cultivation and determination of turbidity

First, 0.5 ml of each of the above-mentioned cultivation solutions of *Lactobacillus bifidus* were inoculated in every 2 of the above-mentioned test media and turbidity was immediately measured with a quartz cell at a wavelength of 660 nm and light path length of 10 mm using a spectrophotometer (Hitachi Seisakusho Co., Ltd.). After the determination, the media were covered with 2 ml sterile liquid paraffin and cultivation was performed for 24 hours in an ordinary incubator at 37° C. Turbidity was measured under the same conditions as previously described at 2-hour intervals and the mean turbidity of the 2 test tubes was calculated as the determination.

Moreover, basic medium containing glucose was simultaneously used as the control and turbidity was similarly determined.

(3) Results of Tests

The test results are shown in FIG. 1. FIG. 1 shows the correlation between cultivation time and the increase in medium turbidity. The axis of abscissas and the axis of ordinates show the cultivation time and the increase in medium turbidity with growth of bacterial bodies, respectively. The figure shows the growth curve of *Bifidobacterium longum* using 4 types of sugar sources with up to 24 hours of cultivation at 37° C. The - - - - - in the figure shows the glucose medium, the —O— shows the raffinose medium, the —△— shows the lactulose medium, and the - - - - - - - shows the isomalto-oligosaccharide medium.

As is clear from FIG. 1, the medium that used raffinose had a higher consumption speed than the medium that used glucose, which is the standard sugar source, the medium that used lactulose has approximately the same sugar consumption speed as the medium that used glucose, and the medium that used isomalto-oligosaccharide had a lower consumption speed than the medium that used glucose. Furthermore, as short a time as possible is preferred as the determination time point so that the bacterial body growth rate will be reflected using the glucose medium as the criterion, but it was concluded that the sugar consumption speed by *Lactobacillus bifidus* can be clearly measured after 8 hours of cultivation.

PRELIMINARY TEST 2

Although various oligosaccharides are known as *Lactobacillus bifidus* growth factor, there are no examples of studies performed in the past on the speed of consumption of the main total oligosaccharides by *Lactobacillus bifidus* under the same cultivation conditions and by the same standards and therefore, the inventors performed comparative assessment of this speed.

(1) Bacteria Strains Tested

Although 10 species of so-called *Lactobacillus bifidus*, which are microorganisms belonging to the genus Bifidobacterium derived from humans, are known today, the following four species, which are known as species that are universal and isolated over a broad range, from infants to adults, in Japan, were submitted to the tests as those that reflect as closely as possible intestinal *Lactobacilluls bifidus*:

*Bifidobacterium bifidum* BB-225, *Bifidobacterium adolescentis* BB-102, *Bifidobacterium breve* BB-308, *Bifidobacterium longum* BB-536.

The inventors also isolated 3 species other than the *Bifidobacterium longum* BB-536 submitted to Preliminary Test 1 from the feces of infants and healthy adults and identified the species, including DNA homology, saccharide availability, etc., by conventional methods, and stored strains whose species could be determined were used. Furthermore, these strains are stored by the inventors and are available for any person when necessary.

(2) Test Method

The basic culture medium and pre-cultivation solution were prepared as in above-mentioned Preliminary Test 1. The test culture medium was prepared using the following 7 types of oligosaccharides, which are widely used as *Lactobacillus bifidus* growth factor, in place of glucose:

Raffinose (Nihon Tensai Seito Co., Ltd.), lactulose (Morinaga Milk Industry Co., Ltd.), galacto-oligosaccharide (Nisshin Seito Co., Ltd.), lactosucrose (Hayashibara Shoji Co., Ltd.), fructo-oligosaccharide (Meiji Seika Co., Ltd.), isomalto-oligosaccharide (Hayashibara Shoji Co., Ltd.), and xylo-oligosaccharide (Santori Co., Ltd.).

Cultivation was performed as in above-mentioned Preliminary Test 1 and the sugar consumption speed was calculated by the following formula and comparative studies were performed, using the increment increase in turbidity of each medium up to 8 hours later as the index.

Consumption speed-accelerating effect (fold)=(increase in turbidity after 8 hours in test medium)/(increase in turbidity after 8 hours in basic medium)

(3) Test Results

The test results are shown in Table 1. When a sugar consumption speed-accelerating effect of 1.0 or higher means that the succharides have the same or stronger *Lactobacilluls bifidus* growth promoting activity as glucose and the succharides are assimilated, no oligosaccharide exceeded this reference value for any of the 4 species tested. The results are characterized in that all four species have relatively strong consumption speed-accelerating activity for lactulose and although raffinose did not show availability for *Bifidobacterium bifidus*, the consumption-speed accelerating activity of the other 3 species of *Lactobacillus bifidus* was highest for raffinose.

Characteristic advantages were seen for several oligosaccharides from these results, but no one single oligosaccharide satisfied the conditions needed as a sugar source for growth of the above-mentioned *Lactobacillus bifidus* and was close to ideal for practical use in order to balance intestinal function.

TABLE 1

| | Test species | | | |
|---|---|---|---|---|
| Oligosaccharide added to test culture medium | Bifidobacterium adolescentis | Bifidobacterium breve | Bifidobacterium bifidum | Bifidobacterium longum |
| Lactulose | 0.97 | 1.08 | 0.96 | 0.92 |
| Lacto-sucrose | 0.83 | 0.87 | 0.03 | 0.78 |
| Raffinose | 1.02 | 1.15 | 0.02 | 1.09 |
| Fructo-oligosaccharides | 0.93 | 0.67 | 0.02 | 0.90 |
| Galacto-oligosaccharide | 0.87 | 0.94 | 0.84 | 0.84 |
| Isomalto-oligosaccharide | 0.79 | 0.87 | 0.00 | 0.63 |
| Xylo-oligosaccharide | 0.89 | 0.53 | 0.49 | 0.67 |

TEST EXAMPLE 1

Next, the inventors performed tests in order to investigate the growth promoting activity of combinations of various types of oligosaccharides on *Lactobacilluls bifidus*. That is, they tested the consumption speed-accelerating effect of 4 species of *Lactobacillus bifidus* by combinations of other oligosaccharides using raffinose, which appears to be the most useful oligosaccharide in terms of availability and the consumption speed of *Lactobacillus bifidus* in the above-mentioned Preliminary Test 2, as the substrate.

(1) Strains Tested

The same four species of *Lactobacillus bifidus* as used in above-mentioned Preliminary Test 2 were employed.

(2) Test Method

The basic culture medium and pre-cultivation solution were prepared as for above-mentioned Preliminary Test 1. The test culture medium was prepared changing the total amount of each of the desired raffinose and oligosaccharide to 2.0% in place of the 2.0% glucose in the basic medium and the addition ratio to 13 steps. The oligosaccharides that were used were the same as in above-mentioned Preliminary Test 2, and cultivation, determination of turbidity and assessment of the sugar consumption speed-accelerating activity were performed by the same methods as in above-mentioned Preliminary Test 2.

(3) Test Results

The consumption speed-accelerating effect of each of the 4 strains of *Lactobaccilus bifidus* tested, as well as the average consumption speed-accelerating effect of the 4 species tested, in a culture medium that used a combination of raffinose and lactulose are shown in Table 2 and the average consumption speed-accelerating effect in each of the 4 species of bacteria tested with various test media other than medium using raffinose and lactulose are shown in Table 3.

As shown in Table 2, good effects in terms of accelerating the consumption speed by *Lactobacilluls bifidus* were obtained when the ratio of raffinose: lactulose ranged from 0.6:1.4 (3:7) to 1.8:0.2 (9:1) with media that used a combination of raffinose and lactulose, and the results were particularly marked within a range of from 1.2:0.8 (3:2) to 1.6:0.4 (4:1).

Moreover, as is clear from the results in Table 3, as in the case of the culture medium that used a combination of raffinose and lactulose, the same or better marked consumption speed-accelerating activity as seen with glucose was obtained from media that used raffinose in combination with either galacto-oligosaccharide or fructo-oligosaccharide. The percentage of these oligosaccharides was almost the same as in the case of lactulose, and it was concluded that a combination of 1 part or more each of galacto-oligosaccharide and fructo-oligosaccharides per 9 parts raffinose is ideal.

It is said that 2 to 3 species of *Lactobaccilus bifidus* are usually present in the human intestines and a high average consumption speed-accelerating activity for the main 4 species of *Lactobaccilus bifidus* derived from humans that were submitted to this Test 1 is an ideal index that reflects the actual state of human intestines.

On the other hand, of the media that used other oligosaccharides, lactosucrose, isomalto-oligosaccharide and xylo-oligosaccharide, media that used a combination of these with raffinose showed better sugar consumption speed-accelerating activity than the media that used the above-mentioned saccharides alone, but marked effects that were the same or better than those with glucose could not be confirmed.

The same tests were performed with a total of 3 or more types of oligosaccharide compositions by mixing 2 or more of lactulose, galacto-oligosaccharide and lacto-oligosaccharide with raffinose, but approximately the same results were obtained.

TABLE 2

| Concentration in culture medium | | Test strain | | | | Mean consumption speed-accelerating activity of 4 species |
|---|---|---|---|---|---|---|
| Raffinose | Lactulose | *B. adolescentis* | *B breve* | *B. bifidum* | *B longum* | |
| (0.0) | (2.0) | (0.97) | (1.08) | (0.96) | (0.92) | (0.98) |
| 0.1 | 1.9 | 0.95 | 0.97 | 0.97 | 0.92 | 0.95 |
| 0.2 | 1.8 | 0.93 | 0.96 | 0.96 | 0.92 | 0.94 |
| 0.4 | 1.6 | 0.98 | 0.97 | 0.93 | 0.96 | 0.96 |
| 0.5 | 1.5 | 1.01 | 1.02 | 0.95 | 0.99 | 0.99 |
| 0.6 | 1.4 | 1.04 | 1.06 | 0.89 | 1.03 | 1.01 |
| 0.8 | 1.2 | 1.06 | 1.06 | 0.86 | 1.00 | 1.00 |
| 1.0 | 1.0 | 1.13 | 1.09 | 0.82 | 1.08 | 1.03 |
| 1.2 | 0.8 | 1.26 | 1.26 | 0.80 | 1.19 | 1.13 |
| 1.4 | 0.6 | 1.21 | 1.36 | 0.77 | 1.22 | 1.14 |
| 1.5 | 0.5 | 1.23 | 1.25 | 0.68 | 1.28 | 1.11 |
| 1.6 | 0.4 | 1.20 | 1.22 | 0.51 | 1.27 | 1.05 |
| 1.8 | 0.2 | 1.18 | 1.19 | 0.43 | 1.20 | 1.00 |
| 1.9 | 0.1 | 1.10 | 1.13 | 0.29 | 1.10 | 0.91 |
| (2.0) | (0.0) | (1.02) | (1.15) | (0.02) | (1.09) | (0.82) |

TABLE 3

| Concentration in culture medium | | Mean consumption speed-accelerating activity of 4 species of test bacteria | | | | |
|---|---|---|---|---|---|---|
| Raffinose | Other oligosaccharide | Galacto-oligosaccharide | Lactosucrose | Lacto-oligosaccharide | Isomalto-oligosaccharide | Xylo-oligosaccharide |
| (0.0) | (2.0) | (0.87) | (0.63) | (0.63) | (0.57) | (0.65) |
| 0.1 | 1.9 | 0.90 | 0.74 | 0.70 | 0.61 | 0.67 |
| 0.2 | 1.8 | 0.91 | 0.75 | 0.77 | 0.64 | 0.70 |
| 0.4 | 1.6 | 0.95 | 0.83 | 0.86 | 0.66 | 0.72 |
| 0.5 | 1.5 | 0.98 | 0.85 | 0.91 | 0.72 | 0.70 |
| 0.6 | 1.4 | 1.01 | 0.89 | 0.96 | 0.71 | 0.75 |
| 0.8 | 1.2 | 1.00 | 0.90 | 0.94 | 0.76 | 0.80 |
| 1.0 | 1.0 | 1.02 | 0.92 | 1.00 | 0.82 | 0.83 |
| 1.2 | 0.8 | 1.11 | 0.93 | 1.06 | 0.83 | 0.88 |
| 1.4 | 0.6 | 1.13 | 0.95 | 1.09 | 0.88 | 0.92 |
| 1.5 | 0.5 | 1.09 | 0.97 | 1.07 | 0.91 | 0.92 |

TABLE 3-continued

Concentration in culture medium

| Raffinose | Other oligo-saccharide | Mean consumption speed-accelerating activity of 4 species of test bacteria | | | | |
|---|---|---|---|---|---|---|
| | | Galacto-oligosaccharide | Lactosucrose | Lacto-oligosaccharide | Isomalto-oligosaccharide | Xylo-oligosaccharide |
| 1.6 | 0.4 | 1.05 | 0.96 | 1.05 | 0.90 | 0.86 |
| 1.8 | 0.2 | 1.00 | 0.92 | 1.01 | 0.88 | 0.83 |
| 1.9 | 0.1 | 0.92 | 0.87 | 0.88 | 0.85 | 0.83 |
| (2.0) | (0.0) | (0.82) | (0.82) | (0.82) | (0.82) | (0.82) |

TEST EXAMPLE 2

This test was performed in order to study the effect of modified milk powder for infants that was produced by the same method as in Example 3 on the fecal characteristics of infants.

(1) Samples and Test Method

The modified milk powder for infants that was produced by the same method as in Example 3 was given for 1 month to 10 infants whose average age was 4 months and the feces of the infants were sampled one month after nursing with this formula and fecal characteristics and intestinal bacteria plexus were tested. Moreover, the feces of 10 infants under approximately the same conditions who had ingested commercial modified milk powder for infants (A Co. Lted.; containing 1.2 g/100 g galacto-oligosaccharide) were sampled and the same items were tested as the control. The tests of intestinal bacteria plexus were performed in accordance with the method of Mitsuoka (Tomoyuki Mitsuoka, "World of Intestinal Bacteria," Sobunsha, 1980), including the method of isolation and cultivation from the feces, etc.

(2) Test Results

The test results are as shown in Table 4. As is clear from Table 4, the characteristics of feces (appearance, water content, color, odor, pH) of infants who had been nursed with modified milk powder containing raffinose and galacto-oligosaccharide had better appearance than the feces taken from infants who had been nursed with commercial modified milk powder, and the intestinal bacteria plexus of the former group showed an increase in *Lactobaccilus bifidus* and a reduction in putrefying bacteria, and there was also a marked increase in the total amount of *Lactobacilluls bifidus* and the ratio of *Lactobacilluls bifidus* accounting for the total intestinal bacteria. This appears to be due to the fact that the desired sugar source is more quickly consumed by the *Lactobacilluls bifidus* widely distributed throughout the intestine than with the conventional product and as a result, *Lactobacillus bifidus* plexus is more quickly formed.

Based on these findings, it was clarified that modified milk powder containing raffinose and galacto-oligosaccharide at a specific ratio plays a role in improving the fecal characteristics and improving intestinal bacteria plexus in infants. Furthermore, no adverse reactions, such as diarrhea, etc., whatsoever were seen with the modified milk powder for infants in Example 3. In addition, although tests were performed with modified milk powder for infants that had been made by other methods, approximately the same findings were obtained.

TABLE 4

| Fecal characteristics | Infants nursed with modified milk powder for infants of Example 3 | Infants nursed with commercial modified milk powder for infants |
|---|---|---|
| Appearance | | |
| Semi-soft | 3/10 infants | 5/10 infants |
| Loose | 7/10 infants | 4/10 infants |
| Watery, diarrhea-like | 0/10 infants | 1/10 infants |
| Color | | |
| Dark yellow to pale yellow | 5/10 infants | 2/10 infants |
| Yellowish green | 3/10 infants | 3/10 infants |
| Green to brown | 2/10 infants | 5/10 infants |
| Smell | | |
| Adult fecal smell | 1/10 infants | 6/10 infants |
| No smell | 5/10 infants | 1/10 infants |
| Acidic smell | 2/10 infants | 3/10 infants |
| Sweet and sour smell | 2/10 infants | 0/10 infants |
| pH | 5.92 | 6.54 |
| Bacteria Plexus | | |
| *Lactobacillus bifidus* | 10.5 (77) | 10.2 (37) |
| Eubacteria | 9.10 (3) | 9.70 (12) |
| Bacteroides | 9.87 (18) | 10.1 (30) |
| Clostridia | 6.12 (0) | 8.38 (1) |
| *Escherichia coli* | 8.67 (1) | 9.78 (14) |
| Staphylococcus | 4.26 (0) | 5.32 (0) |
| Streptococcus | 8.28 (1) | 9.37 (6) |

Note: The number of bacteria is the usual logarithm per 1 g feces and is the mean for 10 infants. The figures in parentheses is the percentage occupied (%).

TETS EXAMPLE 3

This test was performed using a nutritive agent for post-surgical patients that had been prepared by the same method as in Example 4 in order to study the effects an the intestinal putrefaction substance of healthy adults.

(1) Test Method

The nutritive agent for post-surgical patients that is entered in Example 1 was given at 10 g/day for 10 days using as the subjects 20 healthy adults (age 25 to 58 years, mean age of 48 years) and feces were sampled from each subject the day before ingesting the supplement, Day 5 and Day 10 of ingestion, and 10 days after ingestion was completed and the amount of putrefactive substance in the feces was measured. Furthermore, ammonia was measured by colorimetry using an ammonia determination kit (Wako Junyaku Co., Ltd.), and quantitative determination of other putrefactive substances was performed by the method of Yoshihara (Agricultural and Biological Chemistry, vol. 45, p.1873-1875, 1981).

(2) TEST RESULTS

The mean amount of fecal putrefactive substance of the 20 subjects is shown in Table 5. As is clear from Table 5, there was a reduction in the putrefactive substance content of the feces by Day 10 of ingestion in all determinations shown in Table 5, including phenol, indole, skatole, and ammonia, which were the putrefactive substances measured. This shows that the intestinal bacteria plexus changed to *Lactobacillus bifidus*-rich plexus and there was a reduction in putrefying bacteria, including Clostridium, etc., and growth of anaerobic bacteria, such as Peptococcus, Bacteriodes, etc., that participate in the production of ammonia was inhibited.

Consequently, it is clear that by taking the nutritive agent in Example 4, the amount of fecal putrefactive substance is markedly reduced and therefore, this agent has a strong impact on post-surgical nutrition. Furthermore, although agents that were produced by other methods were tested, the same findings were obtained.

TABLE 5

| Putrefactive substance | Before ingestion | Day 5 of ingestion | Day 10 of ingestion | 10 days after ingestion was completed |
|---|---|---|---|---|
| Phenol | 23.5 | 12.1 | 7.3 | 16.7 |
| p-Cresol | 51.2 | 23.8 | 10.9 | 28.2 |
| Ethyl phenol | 13.8 | 8.2 | 5.3 | 8.8 |
| Indole | 14.1 | 7.6 | 5.1 | 10.5 |
| Skatole | 19.2 | 9.5 | 6.4 | 14.0 |
| Ammonia | 193 | 106 | 93 | 159 |

(Note) Units: μg/g feces

EXAMPLE 1

Eight kilograms raffinose (Nihon Tensai Seito Co., Ltd.) and 5 kg lactulose powder (Morinaga Milk Industry Co., Ltd.), as well as 38 kg commercial excipients, viscous agent, etc., were uniformly mixed and filled, 10 g at a time, into aluminum foil bags. The bags were sealed to obtain 5,000 bags of *Lactobacillus bifidus* growth promoting composition.

EXAMPLE 2

Twenty kilograms soy oligosaccharide (Karupisu Shokuhin Kogyo Co., Ltd.; raffinose content of 7%), 0.5 kg lactulose powder (Morinaga Milk Industry Co., Ltd.), 0.5 kg fructo-oligosaccharide (Meiji Seika Co., Ltd.), and 10 g *Lactobacillus bifidus* powder (Morinaga Milk Industry Co., Ltd.; *Lactobacillus bifidus* fungal bodies $10^{10}$/g), as well as a total of 80 kg commercial excipient, such as dextrin, and viscous agent were uniformly mixed and then made into tablets to obtain 100,000 *Lactobacillus bifidus* growth promoting tablets with a content of approximately 1 g per tablet.

EXAMPLE 3

Modified milk powder for infants with the following composition was made by conventional methods:

|  |  | (g/100 g) |
|---|---|---|
| Protein | Casein | 4.2 |
|  | Milk serum protein | 6.2 |
|  | Protein decomposition product | 2.6 |
|  | Amino acids | 0.3 |
| Fats | Modified fats | 24.3 |

EXAMPLE 3-continued

Modified milk powder for infants with the following composition was made by conventional methods:

|  |  | (g/100 g) |
|---|---|---|
| Saccharides | Lactose | 51.4 |
|  | Dextrin | 3.0 |
|  | Raffinose | 0.8 |
|  | Galacto-oligosaccharide | 0.4 |
| Vitamins |  | 2.0 |
| Minerals |  | 2.0 |

Furthermore, raffinose (Nihon Tensai Seito Co., Ltd.), galacto-oligosaccharide (Nisshin Seito Co., Ltd.), and commercial products for all of the others were used.

EXAMPLE 4

Twenty kilograms raffinose (Nihon Tensai Seito Co., Ltd.), 5 kg lactulose powder (Morinaga Milk Industry Co., Ltd.), 50 kg DHA powder (Nihon Yushi Co., Ltd., 100 g egg yolk oil and fat (Kyupi Co., Ltd.), and a total of 20 g vitamins (commercial products, vitamins A, D, E and C) were mixed and filled into aluminum foil bags 15 g at a time. The aluminum bags were sealed to produce 1,600 nutritive agents for post-surgical patients.

Fifteen grams of the above-mentioned nutrititive agent are usually administered to patients twice/day.

EXAMPLE 5

Liquid nutritive agent with the following composition was produced by conventional methods:

|  |  | (g/100 ml) |
|---|---|---|
| Protein | Casein | 4.0 |
|  | Protein decomposition product | 0.5 |
|  | Amino acid | 0.5 |
| Fats | Modified fats | 2.2 |
| Saccharides | Dextrin | 13.5 |
|  | Raffinose | 1.0 |
|  | Fructo-oligosaccharide | 0.5 |
| Vitamins |  | 0.3 |
| Minerals |  | 0.7 |

Furthermore, raffinose (Nihon Tensai Seito Co., Ltd.), fructo-oligosaccharide (Meiji Seika Co., Ltd.), and commercial products for all of the others were used.

INDUSTRIAL APPLICABILITY

As previously explained in detail, the present invention pertains to a *Lactobacilluls bifidus* growth promoting composition which comprises one or 2 or more oligosaccharide selected from lactulose, galacto-oligosaccharide, and fructo-oligosaccharide, and raffinose as its active ingredients, and a blend obtained by mixing said composition and other edible ingredients. The effects of the present invention are as follow:

1) The *Lactobacillus bifidus* growth promoting composition of the present invention is very quickly used by *Lactobacillus bifidus* and is widely assimilated by the main species of intestinal *Lactobacillus bifidus*, and therefore, expresses *Lactobacillus bifidus* growth promoting effects, even though the amount of oligosaccharide to be ingested is small, and furthermore, there is no concern over adverse reaction, such as diarrhea, etc.

2) The *Lactobacillus bifidus* growth promoting composition of the present invention can effectively promote selective intestinal growth of *Lactobacillus bifidus* and thereby inhibit growth of putrefying bacteria.

3) The *Lactobacillus bifidus* growth promoting composition of the present invention maintains fecal characteristics in good condition and inhibits the generation of various putrefactive substances to play a role in health maintenance.

4) The blend of the present invention can be expected to be effective in balancing intestinal function over a broad range of ages, from infants to elderly persons, and therefore, it can be used in modified milk powder, various nutritive agents, and various other food products.

What is claimed is:

1. A growth promoting composition for bacteria belonging to the species of Bifidobacterium selected from the group consisting of *Bifidobacterium adolecentis, Bifidobacterium breve*, and *Bifidobacterium longum*, which comprises a basic bacterial growth medium and 2% by weight of a saccharide mixture consisting of raffinose and lactulose at a ratio of 4:1 to 3:2.

2. A blend, comprising 0.05% by weight or more of the growth promoting composition of claim 1 and other edible ingredients for general foods.

3. The blend of claim 2, wherein said other edible ingredients are ingredients for powdered milk for nursing infants.

4. The blend of claim 2, wherein said other edible ingredients are ingredients for nutritive agents.

5. A growth promoting composition for bacteria belonging to the species of Bifidobacterium selected from the group consisting of *Bifidobacterium adolecentis, Bifidobacterium breve,* and *Bifidobacterium longum,* which comprises a basic bacterial growth medium and 2% by weight of a saccharide mixture consisting of raffinose and galacto-oligosaccharide at a ratio of 4:1 to 3:2.

6. A blend, comprising 0.05% by weight or more of the growth promoting composition of claim 5 and other edible ingredients for general foods.

7. The blend of claim 6, wherein said other edible ingredients are ingredients for powered milk for nursing infants.

8. The blend of claim 6, wherein said other edible ingredients are ingredients for nutritive agents.

9. The growth promoting composition of claim 1, wherein the ratio of raffinose and lactulose is 7:3.

10. The growth promoting composition of claim 1, wherein the ratio of raffinose and lactulose is 3:1.

11. The blend of claim 2, wherein the ratio of raffinose and lactulose is 7:3.

12. The blend of claim 2, wherein the ratio of raffinose and lactulose is 3:1.

13. The growth promoting composition of claim 5, wherein the ratio of raffinose and galacto-oligosaccharide is 7:3.

14. The growth promoting composition of claim 5, wherein the ratio of raffinose and galacto-oligosaccharide is 3:1.

15. The blend of claim 6, wherein the ratio of raffinose and galacto-oligosaccharide is 7:3.

16. The blend of claim 6, wherein the ratio of raffinose and galacto-oligosaccharide is 3:1.

17. A method of growing Bifidobacterium selected from the group consisting of *Bifidobacterium adolecentis, Bifidobacterium breve,* and *Bifidobacterium longum in vitro,* comprising culturing Bifidobacterium with a growth promoting composition which comprises a basic bacterial growth medium and 2% by weight of a saccharide mixture consisting of raffinose and lactulose in a ratio of 4:1 to 3:2.

18. The method according to claim 17, comprising culturing Bifidobacterium under anaerobic conditions.

19. The method according to claim 17, comprising culturing Bifidobacterium under anaerobic conditions for at least 24 hours.

20. The method according to claim 17, wherein the ratio of raffinose and lactulose is 7:3.

21. The method according to claim 17, wherein the ratio of raffinose and lactulose is 3:1.

22. A method of growing Bifidobacterium selected from the group consisting of *Bifidobacterium adolecentis, Bifidobacterium breve,* and *Bifidobacterium longum in vitro,* comprising culturing Bifidobacterium with a growth promoting composition which comprises a basic bacterial growth medium and 2% by weight of a saccharide mixture consisting of raffinose and galacto-oligosaccharide in a ratio of 4:1 to 3:2.

23. The method according to claim 22, comprising culturing Bifidobacterium under anaerobic conditions.

24. The method according to claim 22, comprising culturing Bifidobacterium under anaerobic conditions for at least 24 hours.

25. The method according to claim 22, wherein the ratio of raffinose and galacto-oligosaccharide is 7:3.

26. The method according to claim 22, wherein the ratio of raffinose and galacto-oligosaccharide is 3:1.

* * * * *